US008034362B2

(12) United States Patent
Thomas et al.

(10) Patent No.: US 8,034,362 B2
(45) Date of Patent: Oct. 11, 2011

(54) CHEMICAL COMPOSITION OF HYDROGELS FOR USE AS ARTICULATING SURFACES

(75) Inventors: Brian H. Thomas, Columbia City, IN (US); Donald L. Yakimicki, Warsaw, IN (US); Steven Charlebois, Goshen, IN (US); Laura L. Borgstede, Fort Wayne, IN (US); Niels Abt, Winterthur (CH); James J. Mason, Granger, IN (US); Oludele Popoola, Granger, IN (US)

(73) Assignee: Zimmer, Inc., Warsaw, IN (US)

( * ) Notice: Subject to any disclaimer, the term of this patent is extended or adjusted under 35 U.S.C. 154(b) by 359 days.

(21) Appl. No.: 11/969,591

(22) Filed: Jan. 4, 2008

(65) Prior Publication Data

US 2009/0175919 A1 Jul. 9, 2009

(51) Int. Cl.
*A61L 27/14* (2006.01)
*C08F 120/10* (2006.01)
*C08F 116/06* (2006.01)
(52) U.S. Cl. .................. 424/423; 525/50; 526/319
(58) Field of Classification Search .................. None
See application file for complete search history.

(56) References Cited

U.S. PATENT DOCUMENTS

| | | | |
|---|---|---|---|
| 3,200,178 A | 8/1965 | Kanji |
| 3,862,265 A | 1/1975 | Steinkamp |
| 3,875,302 A | 4/1975 | Inoue |
| 4,036,788 A | 7/1977 | Steckler |
| 4,058,491 A | 11/1977 | Steckler |
| 4,060,678 A | 11/1977 | Steckler |
| 4,071,508 A | 1/1978 | Steckler |
| 4,279,795 A | 7/1981 | Yamashita |
| 4,300,820 A | 11/1981 | Shah |
| 4,379,874 A | 4/1983 | Stoy |
| 4,451,599 A | 5/1984 | Odorzynski |
| 4,451,630 A | 5/1984 | Atkinson |
| 4,464,438 A | 8/1984 | Lu |
| 4,472,542 A | 9/1984 | Nambu |
| 4,640,941 A | 2/1987 | Park |
| 4,656,216 A | 4/1987 | Muller et al. |
| 4,663,358 A | 5/1987 | Hyon |
| 4,664,857 A | 5/1987 | Nambu |
| 4,699,146 A | 10/1987 | Sieverding |
| 4,734,097 A | 3/1988 | Tanabe |
| 4,771,089 A | 9/1988 | Ofstead |
| 4,772,287 A | 9/1988 | Ray |
| 4,808,353 A | 2/1989 | Nambu |
| 4,842,597 A | 6/1989 | Brook |
| 4,851,168 A | 7/1989 | Graiver |
| 4,859,719 A | 8/1989 | Ofstead |
| 4,871,490 A | 10/1989 | Rosiak |
| 4,874,562 A | 10/1989 | Hyon |
| 4,915,974 A | 4/1990 | D'Amelia |
| 4,956,122 A | 9/1990 | Watts et al. |
| 4,966,924 A | 10/1990 | Hyon |
| 4,988,761 A | 1/1991 | Ikada |
| 5,028,648 A | 7/1991 | Famili |
| 5,047,055 A | 9/1991 | Bao |
| 5,053,455 A | 10/1991 | Kroggel |
| 5,106,876 A | 4/1992 | Kawamura |
| 5,118,779 A | 6/1992 | Szycher |
| 5,122,565 A | 6/1992 | George |
| 5,157,093 A | 10/1992 | Harisiades |
| 5,189,097 A | 2/1993 | LaFleur |
| 5,192,326 A | 3/1993 | Bao |
| 5,244,799 A | 9/1993 | Anderson |
| 5,276,079 A | 1/1994 | Duan et al. |
| 5,288,503 A | 2/1994 | Wood |
| 5,306,311 A | 4/1994 | Stone |
| 5,311,223 A | 5/1994 | Vanderlaan |
| 5,315,478 A | 5/1994 | Cadwell |
| 5,334,634 A | 8/1994 | Bastiolo |
| 5,336,551 A | 8/1994 | Graiver et al. |
| 5,358,525 A | 10/1994 | Fox |
| 5,360,830 A | 11/1994 | Bastiolo |
| 5,362,803 A | 11/1994 | LaFleur |
| 5,364,547 A | 11/1994 | Babb et al. |
| 5,407,055 A | 4/1995 | Tanaka |

(Continued)

FOREIGN PATENT DOCUMENTS

EP 0256293 2/1988

(Continued)

OTHER PUBLICATIONS

Tripathy et al. "Novel Flocculating Agent Based on Sodium Aglignate and Acrylamide." European Polymer Journal 35 (1999) 2057-2072.*
Noguchi et al., Poly(vinyl Alcohol) Hydrogel as an Artificial Articular Cartilage; Evaluation of Biocompatibility, Journal of Applied Biomaterials, vol. 2, 101-107 (1991), John Wiley & Sons, Inc.
"Glossary of Basic Terms in Polymer Science," published by the International Union of Pure and Applied Chemistry, Pure Appl. Chem. 68, 2287-2311 (1996 IUPAC), Great Britain.
Babb D.A., et al., Perfluorocycleobutaine Aromatic Ether Polymers. III. Synthesis and Thermal Stability of a Thermoset Polymer Containing Triphenylphosphine Oxide, Journal of Applied Polymer Science, vol. 69 (1998), pp. 2005-2012, John Wiley and Sons Inc.

(Continued)

*Primary Examiner* — Robert A Wax
*Assistant Examiner* — Danah Al-Awadi
(74) *Attorney, Agent, or Firm* — Cook Alex Ltd.

(57) ABSTRACT

The present invention provides a hydrogel composition comprising at least one polymer with functional groups including alcohol groups, acid groups, and amide groups and where the ratio of the functional alcohol groups to functional acid groups in the hydrogel composition ranges from about 16:1 to about 3:2. The present invention also provides a method of repairing an articulating surface in a body using the inventive composition. The inventive hydrogel composition is created by blending two or more polymers to achieve the desired ratio of functional groups, reacting at least one polymer with a reagent that results in the formation of alcohol, acid, and/or amide functional groups of the desired ratio, and/or polymerizing at least one monomer to achieve the desired ratio of functional groups.

19 Claims, No Drawings

U.S. PATENT DOCUMENTS

| | | |
|---|---|---|
| 5,409,966 A | 4/1995 | Duan et al. |
| 5,410,016 A | 4/1995 | Hubbell |
| 5,458,643 A | 10/1995 | Oka |
| 5,527,271 A | 6/1996 | Shah |
| 5,540,033 A | 7/1996 | Fox et al. |
| 5,552,096 A | 9/1996 | Auda |
| 5,576,072 A | 11/1996 | Hostettler et al. |
| 5,580,938 A | 12/1996 | Gutweiler |
| 5,624,463 A | 4/1997 | Stone |
| 5,632,774 A | 5/1997 | Babian |
| 5,674,295 A | 10/1997 | Ray |
| 5,681,300 A | 10/1997 | Ahr |
| 5,705,296 A | 1/1998 | Kamauchi et al. |
| 5,709,854 A | 1/1998 | Griffith-Cima |
| 5,711,960 A | 1/1998 | Shikinami |
| 5,716,404 A | 2/1998 | Vacanti |
| 5,723,331 A | 3/1998 | Tubo et al. |
| 5,834,029 A | 11/1998 | Bellamkonda |
| 5,879,713 A | 3/1999 | Roth et al. |
| 5,891,826 A | 4/1999 | Tsaur et al. |
| 5,941,909 A | 8/1999 | Purkait |
| 5,976,186 A | 11/1999 | Bao |
| 5,981,826 A | 11/1999 | Ku |
| 6,015,576 A | 1/2000 | See |
| 6,017,577 A | 1/2000 | Hostettler |
| 6,040,493 A | 3/2000 | Cooke |
| 6,080,488 A | 6/2000 | Hostettler |
| 6,117,449 A | 9/2000 | See |
| 6,120,904 A | 9/2000 | Hostettler |
| 6,121,341 A | 9/2000 | Sawhney |
| 6,129,761 A | 10/2000 | Hubbell |
| 6,132,468 A | 10/2000 | Mansmann |
| 6,139,963 A | 10/2000 | Fujii |
| 6,146,686 A | 11/2000 | Leitao |
| 6,156,345 A | 12/2000 | Chudzik |
| 6,156,572 A | 12/2000 | Bettamkonda |
| 6,162,456 A | 12/2000 | Dunbar |
| 6,180,132 B1 | 1/2001 | Huang |
| 6,180,606 B1 | 1/2001 | Chen et al. |
| 6,184,197 B1 | 2/2001 | Heinzman et al. |
| 6,187,048 B1 | 2/2001 | Mitner |
| 6,207,185 B1 | 3/2001 | See |
| 6,211,296 B1 | 4/2001 | Frate |
| 6,224,893 B1 | 5/2001 | Langer |
| 6,231,605 B1 | 5/2001 | Ku |
| 6,232,406 B1 | 5/2001 | Stoy |
| 6,238,691 B1 | 5/2001 | Huang |
| 6,268,405 B1 | 7/2001 | Yao |
| 6,271,278 B1 | 8/2001 | Park |
| 6,280,475 B1 | 8/2001 | Bao |
| 6,306,424 B1 | 10/2001 | Vyakarnam |
| 6,365,149 B2 | 4/2002 | Vyakarnam |
| 6,371,984 B1 | 4/2002 | Van Dyke |
| 6,372,283 B1 | 4/2002 | Shim |
| 6,375,634 B1 | 4/2002 | Carroll |
| 6,387,325 B1 | 5/2002 | Keusch |
| 6,402,784 B1 | 6/2002 | Wardlaw |
| 6,443,988 B2 | 9/2002 | Felt |
| 6,509,098 B1 | 1/2003 | Merrill |
| 6,531,147 B2 | 3/2003 | Sawhney |
| 6,533,817 B1 | 3/2003 | Norton |
| 6,583,219 B2 * | 6/2003 | Won et al. .................. 525/54.2 |
| 6,602,952 B1 | 8/2003 | Bentley et al. |
| 6,608,117 B1 | 8/2003 | Gvozdic |
| 6,620,196 B1 | 9/2003 | Trieu |
| 6,626,945 B2 | 9/2003 | Simon |
| 6,629,997 B2 | 10/2003 | Mansmann |
| 6,630,457 B1 | 10/2003 | Aeschlimann |
| 6,632,246 B1 | 10/2003 | Simon |
| 6,645,517 B2 | 11/2003 | West |
| 6,692,738 B2 | 2/2004 | MacLaughlin |
| 6,706,690 B2 | 3/2004 | Reich |
| 6,709,668 B2 | 3/2004 | Won |
| 6,710,104 B2 | 3/2004 | Haraguchi |
| 6,710,126 B1 | 3/2004 | Hirt |
| 6,723,781 B1 | 4/2004 | Frate |
| 6,730,298 B2 | 5/2004 | Griffith-Cima |
| 6,733,533 B1 | 5/2004 | Lozier |
| 6,780,840 B1 | 8/2004 | DeVore |
| 6,783,546 B2 | 8/2004 | Zucherman |
| 6,783,721 B2 | 8/2004 | Higham |
| 6,803,420 B2 | 10/2004 | Cleary |
| 6,852,772 B2 | 2/2005 | Muratoglu |
| 6,855,743 B1 | 2/2005 | Gvozdic |
| 6,861,067 B2 | 3/2005 | McGhee |
| 7,235,592 B2 | 6/2007 | Muratoglu |
| 7,531,000 B2 * | 5/2009 | Hodorek ............... 623/14.12 |
| 2001/0026810 A1 | 10/2001 | McGhee |
| 2001/0032019 A1 | 10/2001 | Van Dyke |
| 2001/0049417 A1 | 12/2001 | Frate |
| 2001/0053897 A1 | 12/2001 | Frate |
| 2002/0022884 A1 | 2/2002 | Mansmann |
| 2002/0026244 A1 | 2/2002 | Trieu |
| 2002/0029083 A1 | 3/2002 | Zucherman |
| 2002/0049498 A1 | 4/2002 | Yuksel |
| 2002/0131952 A1 | 9/2002 | Hennink et al. |
| 2002/0151979 A1 | 10/2002 | Lambrecht |
| 2002/0173855 A1 | 11/2002 | Mansmann |
| 2002/0193531 A1 | 12/2002 | Stoy |
| 2003/0008396 A1 | 1/2003 | Ku |
| 2003/0065389 A1 | 4/2003 | Petersen |
| 2003/0080465 A1 | 5/2003 | Higham |
| 2003/0099709 A1 | 5/2003 | Shah et al. |
| 2003/0130427 A1 | 7/2003 | Cleary |
| 2003/0152528 A1 | 8/2003 | Singh et al. |
| 2003/0170308 A1 | 9/2003 | Cleary |
| 2003/0195628 A1 | 10/2003 | Bao |
| 2003/0232895 A1 | 12/2003 | Omidian |
| 2003/0236323 A1 | 12/2003 | Ratner |
| 2004/0002764 A1 | 1/2004 | Gainor |
| 2004/0005423 A1 | 1/2004 | Dalton et al. |
| 2004/0030392 A1 | 2/2004 | Lambrecht |
| 2004/0039447 A1 | 2/2004 | Simon |
| 2004/0092653 A1 | 5/2004 | Ruberti |
| 2004/0096509 A1 | 5/2004 | Hutchens |
| 2004/0116641 A1 | 6/2004 | Mather |
| 2004/0121951 A1 | 6/2004 | Rhee |
| 2004/0127618 A1 | 7/2004 | Ulmer |
| 2004/0127992 A1 | 7/2004 | Sehman |
| 2004/0131582 A1 | 7/2004 | Grinstaff |
| 2004/0133280 A1 | 7/2004 | Trieu |
| 2004/0143329 A1 | 7/2004 | Ku |
| 2004/0147673 A1 | 7/2004 | Calabro |
| 2004/0153163 A1 | 8/2004 | Posner |
| 2004/0161444 A1 | 8/2004 | Song |
| 2004/0171740 A1 | 9/2004 | Ruberti |
| 2004/0199250 A1 | 10/2004 | Fell |
| 2004/0220296 A1 | 11/2004 | Lowman |
| 2004/0242770 A1 | 12/2004 | Feldstein |
| 2004/0244978 A1 | 12/2004 | Shaapour |
| 2005/0004560 A1 | 1/2005 | Cox |
| 2005/0027069 A1 | 2/2005 | Rhee |
| 2005/0048103 A1 | 3/2005 | Cleary |
| 2005/0049365 A1 | 3/2005 | Cleary |
| 2005/0075454 A1 | 4/2005 | Plochocka et al. |
| 2005/0095296 A1 | 5/2005 | Lowman |
| 2005/0107561 A1 | 5/2005 | Lee et al. |
| 2005/0197441 A1 | 9/2005 | Shibutani |
| 2006/0078587 A1 | 4/2006 | Leong |
| 2006/0141002 A1 | 6/2006 | Liu et al. |
| 2006/0188487 A1 | 8/2006 | Thomas |
| 2007/0004861 A1 | 1/2007 | Cai |
| 2007/0202323 A1 | 8/2007 | Kleiner et al. |
| 2007/0293651 A1 | 12/2007 | Tada |
| 2008/0090145 A1 | 4/2008 | Hiwara |
| 2009/0053318 A1 | 2/2009 | Tan et al. |

FOREIGN PATENT DOCUMENTS

| | | |
|---|---|---|
| EP | 0290616 | 11/1988 |
| EP | 0365108 | 4/1990 |
| EP | 0505634 | 9/1992 |
| EP | 0696210 | 2/1996 |
| EP | 0738762 | 4/1996 |
| EP | 0784987 | 7/1997 |
| EP | 0835143 | 4/1998 |
| EP | 0845480 | 6/1998 |
| EP | 0927053 | 7/1999 |

| | | |
|---|---|---|
| EP | 1079224 | 2/2001 |
| EP | 1174463 | 1/2002 |
| EP | 1593400 | 11/2005 |
| EP | 1595899 | 11/2005 |
| FR | 2786400 | 6/2000 |
| FR | 2 866 571 | 8/2005 |
| FR | 2865939 | 8/2005 |
| FR | 2866571 | 8/2005 |
| GB | 2338958 | 1/2000 |
| JP | 01178545 | 7/1989 |
| JP | 01305959 | 12/1989 |
| JP | 03141957 | 6/1991 |
| JP | 04303444 | 10/1992 |
| JP | 09124730 | 5/1997 |
| JP | 09124731 | 5/1997 |
| JP | 10036524 | 2/1998 |
| JP | 10036534 | 2/1998 |
| JP | 10043286 | 2/1998 |
| JP | 10306534 | 2/1998 |
| WO | 90/15082 A1 | 12/1990 |
| WO | WO 94/13235 | 6/1994 |
| WO | 9417851 | 8/1994 |
| WO | WO/95/02616 | 1/1995 |
| WO | 9526699 | 10/1995 |
| WO | 9640304 | 4/1998 |
| WO | 9817215 | 4/1998 |
| WO | 9853768 | 12/1998 |
| WO | 9903454 | 1/1999 |
| WO | 9913923 | 3/1999 |
| WO | 9907320 | 12/1999 |
| WO | WO 99/67320 | 12/1999 |
| WO | 0117574 | 3/2001 |
| WO | WO 01/19283 | 3/2001 |
| WO | 0177197 | 10/2001 |
| WO | WO 02/04570 | 1/2002 |
| WO | 0213871 | 2/2002 |
| WO | 02060501 | 8/2002 |
| WO | 02087642 | 11/2002 |
| WO | 02087645 | 11/2002 |
| WO | 03008007 | 1/2003 |
| WO | 03074099 | 9/2003 |
| WO | WO/03/082359 | 10/2003 |
| WO | 2004007651 | 1/2004 |
| WO | 2004029174 | 4/2004 |
| WO | 2004031253 | 4/2004 |
| WO | 2004047690 | 6/2004 |
| WO | 2004055057 | 7/2004 |
| WO | 2004060427 | 7/2004 |
| WO | 2004063388 | 7/2004 |
| WO | 2004064693 | 8/2004 |
| WO | 2004066704 | 8/2004 |
| WO | 2004069296 | 8/2004 |
| WO | 2004069296 A1 | 8/2004 |
| WO | 2004072138 | 8/2004 |
| WO | 2004093786 | 11/2004 |
| WO | 2005004943 | 1/2005 |
| WO | 2005035726 | 4/2005 |
| WO | WO/2005/030382 | 4/2005 |
| WO | WO 2005/030832 | 4/2005 |
| WO | 2006021054 | 3/2006 |
| WO | 2006091706 | 8/2006 |
| WO | WO/2007/067697 | 6/2007 |
| WO | 2007015208 | 8/2007 |
| WO | WO 2008/144514 | 11/2008 |
| WO | WO/2009/020793 | 2/2009 |
| WO | WO/2009/032430 | 3/2009 |
| WO | WO/2009/088654 A3 | 5/2010 |

OTHER PUBLICATIONS

Peppas, et al., Physicochemical Foundations and Structural Design of Hydrogels in Medicine and Biology, Annu. Rev. Biomed. Eng. 2000, 02:9-29.

Hassan, et al., Structure and Applications of Poly(vinyl alcohol) Hydrogels Produced by Conventional Crosslinking or by Freezing/Thawing Methods, Advances in Polymer Science, vol. 153, Springer-Verlag Berlin Heidelberg 2000.

Bryant, S.J. et al. "Crosslinking Density Influences Chondrocyte Metabolism in Dynamically Leaded Photocrosslinked Poly(ethylene glycol) Hydrogels." Ann. Biomed. Eng., Mar. 2004, pp. 407-417, vol. 3, No. 3.

Bryant, S.J. et al. "The Effects if Scaffold thickness on Tissue Engineered Cartilage in Photocrosslinked Poly (ethylene oxide) hydrogels." Biomaterials 22, 2001, pp. 619-628.

Bryant, S.J. et al. "Photocrosslinkable Poly(ethylene oxide) and Poly (vinyl alcohol) Hydrogels for Tissue Engineering Cartilage." 21st Annual Conference and the 1999 Annual Fall Meeting of the Biomedical Engineering Society, Oct. 13-15, 1999, Atlanta, GA; Engineering in Medicine and Biology 1999, p. 751, vol. 2.

Durmaz, S. et al. "Phase Separation during the Formation of Poly(acrylamide) Hydrogels" Polymer 41, 2000, pp. 5729-5735.

Gong, J.P. et al. "Friction of Polymer Gels and the Potential Application as Artificial Cartilage." SPIE, Mar. 1999, pp. 218-225, vol. 3669.

Guilherme, R. et al. "Hydrogels based on PAAm network with PNIPAAm included: hydrophilic-hydrophobic transition measured by the partition of Organe II and Methylene Blue in Water." Polymer 44, 2003, pp. 4213-4219.

Hassan, C.M. et al. "Modeling of Crystal Dissolution of Poly(vinyl alcohol) gels produced by freezing/thawing processes." Polymer 41, 2000, pp. 6729-6739.

Hassan, C.M. et al. "Structure and Morphology of Freeze/Thawed PVA Hydrogels," Macromolecules, 2000, pp. 2472-2479, vol. 33, No. 7.

Hickey, A.S. et al. "Solute Diffusion in Poly(vinyl) alcohol/poly(acrylic) acid composite membranes prepared by freezing/thawing techniques." J. Memb. Sci. 107, 1995, pp. 229-237.

Kobayashi, M. et al. "Development of an Artificial Meniscus Using Polyvinyl alcohol-hydrogel for early return to, and continuance of, athletic life in sportspersons with severe meniscus injury." Abstract only, The Knee 10, 2003, p. 53.

Kobayashi, M. et al. "Preliminary Study of Polyvinylalcohol-hydrogel (PVA-H) artificial meniscus." Biomaterials 24, 2003, pp. 639-647.

Lester, C.L. et al. "Physical Properties of Hydrogels Synthesized from Lyotropic Liquid Crystalline Templates" Chem. Mater. 15, 2003, pp. 3376-3384.

Mano, V. et al. "Blends Composed of Poly(N-Isopropylacrylamide) and an Ethylene/Vinyl Alcohol Copolymer: Thermal and Morphological Studies" J. App. Polymer Sci., 2004, pp. 501-505.

Park, J.H. et al. "Hydrogels based on Poly(ethylene oxide) and poly (tetramethylene oxide) or poly)dimethyl siloxane). III. In vivo Biocompatability and Biostability." J. Biomed. Mater. Res. 64A, 2003, pp. 309-319.

Schmedlen, R.H. et al. "Photocrosslinkable polyvinyl alcohol hydrogels that can be modified with cell adhesion peptides for use in tissue engineering." Biomaterials, 23, 2002, pp. 4325-4332.

Suggs, L.J. et al. "In vitro Cytotoxicity and In Vivo Biocompatability of Poly(propylene fumarate-co-ethylene glycol) hydrogels." J. Biomed. Mater. Res., 1999, pp. 22-32, vol. 46.

Thomas, J.D. "Novel Associated PVA/PVDP Hydrogels for Nucleuc Pulposus Replacement." Thesis, Master of Science in Material Engineering Degree, Drexel University, Sep. 2001.

Ushio, K. et al. "Attachment of Artificial Cartilage to Underlying Bone." J. Biomed. Mater. Res. Part B: Appl. Biomater. 68B, 2004, pp. 59-68.

Ushio, K. et al. "Partial Hemiarthroplasty for the treatment of Osteonecrosis of the Femoral Head: An Experimental Study in the Dog." J. Bone Joint Surg., 2003, pp. 922-930, vol. 85B.

Zhang, X. et al. "Synthesis and Characterization of Partially Biodegradable, Temperature and pH Sensitive Dex-MA/PNIPAAm Hydrogels." Biomat., 25, 2004, pp. 4719-4730.

"Lecture 7: Hydrogel Biomaterials: Structure and Physical Chemistry," Spring 2003, 8 pages.

ISR/WO for PCT/US2006/006356 dated Jun. 22, 2006, 9 pages.

EP Search Report for EP06255568.5, Jun. 15, 2007.

Rao et al. J. Chem. Soc. Dalton Trans., 2001, 1939-1944.

Li et al. Anal. Biochem., 256, 130-132 (1998).

Anseth et al. "In situ forming degradable networks and their application in tissue engineering and drug delivery." J. Controlled Release 78 (2002), 199-209, 2002.

Lin-Gibson et al. "Synthesis and Characterization of PEG Dimethacrylates and Their Hydrogels." Biomacromolecules 2004, 5, 1280-1287, 2004.

Peppas et al. Structure and Applications of Poly(vinyl alcohol) Hydrogels Produced by Conventional Crosslinking or by Freezing/Thawing Methods. Adv. Polymer Sci. 153, 37 (2000).

LeGeros R. Z., "Calcium phosphates in oral biology and medicine," Monograph in Oral Science, vol. 15, pp. 1-201, 1991.

Chow et al.,"Octacalcium Phosphate," Monograph in Oral Science, vol. 18, pp. 94-112 and 130-148, 2001.

Carey et al., Adv. Org. Chem., Part B., p. 892, 2001.

Hassan et al. "Cellular PVA Hydrogels Produced by Freeze/Thawing." J. Appl. Poly. Sci. 76, 2075 (2000).

Moro et. al. "Surface Grafting of Artificial Joints with Biocompatible Polymer for Preventing Periprosthetic Osteolysis." Nature Materials, 3, 829 (2004).

Hickey et al. :Solute Diffusion in Poly(vinyl)alchohol/poly(acrylic acid) composite membranes prepared by freezing/thawing techniques. Polymer 38, pp. 5931-5936 (1997).

Wang B., et al. The Influence of Polymer concentration on the Radiation-chemical Yield of Intermolecular Crosslinking of Poly(Vinyl Alcohol) by gamma-rays in Deoxygenated Aqueous Solution. Radiation Physics and Chemistry, 2000. 59: p. 91-95.

Rosiak, J. M. & Ulanski, P. Synthesis of hydrogels by irradiation of polymers in aqueous solution, Radiation Physics and Chemistry 1999 55: 139-151.

Stammen, J. A., et al. Mechanical properties of a novel PVA hydrogel in shear and unconfined compression Biomaterials, 2001 22: p. 799-806.

Yamaura, K., et al. Properties of gels obtained by freezing/thawing of poly(vinyl alcohol)/water/dimethyl sulfoxide solutions. Journal of Applied Polymer Science 1989 37:2709-2718.

Lozinsky, V. I. and Damshkaln, L. G. Study of cryostructuration of polymer systems. XVII. Poly(vinyl alcohol) cryogels: Dynamics of cryotropic gel formation. Journal of Applied Polymer Science 2000 77:2017-2023.

Oka M et al. "Development of artificial articular cartilage," Pro. Inst. Mech. Eng. 2000 214:59-68.

EP Search Report for EP 06256525.4 dated May 20, 2007.

ISR/WO for PCT/EP2005/010931 dated Feb. 16, 2006.

ISR/WO for PCT/US2007/064782 dated May 3, 2008.

EP Search Report for EP06256452.1 dated May 23, 2007.

ISR/WO for PCT/US2006/046725 dated Jul. 28, 2008.

Park K.R. et al. "Synthesis of PVA/PVP Hydrogels having Two-Layer by Radiation and their Physical Properties." Rad. Phys. and Chem., Jun. 2003, pp. 361-365. vol. 67, No. 3-4.

Hassan C.M. "Diffusional Characteristics of Freeze/Thawed Poly(vinyl alcohol) hydrogels: Applications to protein controlled release from multilaminate devices." Eur. J. Pharm. and Biopharm., 2000, pp. 161-165, vol. 49.

Bass L.S. "Laser Tissue Welding: A Comprehensive Review of Current and Future Clinical Applications," Lasers in Surgery and Medicine, 1995, pp. 315-349. vol. 17.

Search Report for PCT/US2008/071435 dated Feb. 2, 2009.

Bray, J.C. et al. "Poly(vinyl Alcoohol) Hydrogels: Formation by Eelctron Beam Irradiation of Aqueous Solutions and Subsequent Crystallization." J. Applied Polymer Sci., vol. 17, pp. 3779-3794, 1973.

Bray, J.C. et al. "Poly(vinyl Alcohol) Hydrogels for Synthetic Articular Cartilage Material," Biomed. Mater. Res., vol. 7, pp. 431-443, 1973.

Kawanishi, K. Thermodynamic Consideration of the Sol-Gel Transition in Polymer Solutions. 35th Annual Meeting of the Society of Polymer Science, Japan 1986.

Lozinsky, V.I. et al. "Study of Cryostructures of Polymer Systems, XIV. Poly(vinyl alcohol) Cryogels: Apparent Yield of Freeze-Thaw Induced Gelation of Concentrated Aqueous Solutions of the Polymer." J. Applied Polymer Sci., vol. 77, 1822,1831 (2000).

Lozinsky, V.I. et al. "Study of Cryostructuration of Polymer Systems, XVII. Poly(vinyl alcohol) Cryogels: Dynamics of the Cryotropic Gel Formation." J. Appl. Polymer Sci., vol. 77, 2017-2023 (2000).

Lozinsky, V.I. et al. "Swelling Behavior of poly (vinyl alcohol) cryogels employed as matrices for cell immobilization." Enzyme Microb. Technol., vol. 18, Issue 8, Jun. 1996, pp. 561-569.

Peppas et al. "Reinforced Uncrosslinkable Poly (vinyl alcohol) gels produced by cyclic freezing-thawing processes: A Short Review." J. Controlled Release, 16 (1991), 305-310.

Mondino, A.V. et al. "Physical properties of gamma irradiated poly (vinyl alcohol) hydrogel preparations" Radiation Physics and chemistry, 55, p. 723,726 (1999).

Urushizaki, F. Swelling and Mechanical Properties of Poly (vinyl alcohol) Hydrogels. Intl. J. Pharma., 58, 135-142, 1990.

Lozinsky, V.I. "On the Possibility of Mechanodestruction of Poly (vinyl Alcohol) Molecules under Moderate Freezing of its Concentrated Water Solutions." Polymer Bulletin, 15, p. 333-340 (1986).

Yokoyama, F. "Morphology and Structure of Highly Elastic Poly (vinyl alcohol) Hydrogel Prepared by Repeated Freezing-and-Melting" Colloid & Polymer Sci. 264, 595-601 (1986).

Covert, R.J. et al. "Friction and Wear Testing of a New Biomaterial for Use as an Articular Cartilage Substitute," BED 50 (2001), 355-356, Bioengineering Conference, ASME 2001.

Ding, Mei Yee. Characterisation of Polyvinyl Alcohol Hydrogels, 2003. Undergraduate Chemical Engineering Thesis, University of Queensland, Brisbane QLD 4072, Australia http://www.cheque.uq.edu.au/ugrad/theses/2003/pdf/CHEE4006/40054522/40054522.pdf (working link on 04/20/2009).

Jaguar-Grodzinski, J. "Biomedical Application of Functional Polymers." Reactive and Functional Polymers 39 (1999) 99-138.

Ulanski, P. et al. "Oh-Radical induced crosslinking and strand breakage of poly (vinyl alcohol) in aqueous solution in the absence and presence of oxygen. A pulse radiolysis and product study" Macromol. Chem. Phys. 195, p. 1443-14461 (1994).

Carey et al., Adv. Org. Chem., Part B., p. 829, 2001.

Chow et al., "Octacalcium Phosphate," Monograph in Oral Science, vol. 18, pp. 94-111 and 130-147, 2001.

LeGeros R. Z., "Calcium Phosphates in Oral Biology and Medicine," Monograph in Oral Science, vol. 15, pp. 1-201, 1991.

Hickey et al., "Mesh Size and Diffusive Characteristics of Semicrystalline . . . ", Journal of Membrane Science 107 (1995) pp. 229-237.

Green, Mark, et al., Organic Chemistry Principles and Industrial Practice, Wiley VCH, 2003.

Haralabakopoulus, A. et al., "Modification of Poly(vinyl alcohol) Polymers by Aliphatic Carboxylic Acids via Reactive Blending," Journal of Applied Polymer Science, vol. 69, pp. 1885-1890, 1998.

Lu. Sanxiu, et al., "Photopolymerization of multilaminated poly(HEMA) hydrogels for controlled release," Journal of Controlled Release, vol. 57, pp. 291-300, 1999.

Taguchi, Tetsushi, et al, "Hydroxyapatite Formation on/in Poly(vinyl alcohol) Hydrogel Matrices Using a Novel Alternate Soaking Process," Chemistry Letters, pp. 711-712, 1998.

West, Jennifer, et al, "Photopolymerized hydrogel materials for drug delivery applications," Reactive Polymers, vol. 25, pp. 139-147, 1995.

EP Search Report for EP Application No. 050010009.9-2115 dated Mar. 1, 2005.

Preliminary Report on Patentability & Written Opinion for PCT/US2008/071539 dated Mar. 2, 2010, 6 pgs.

Preliminary Report on Patentability from PCT/US2008/071435 dated Feb. 9, 2010.

Search Report for PCT/US2008/071435 dated Feb. 12, 2009.

EPO Invitation to Pay additional fees and Annex to Search Report for PCT/US2006/046725 dated Apr. 22, 2008, 8 pages.

Search Report and Written Opinion for PCT/US2008/083213 dated May 8, 2009.

Preliminary Report on Patentability & Written Opinion for PCT/US2006/006356 dated Aug. 28, 2007.

PCT International Preliminary Report on Patentability and Written Opinion for PCT/US2008/086817 dated Jul. 6, 2010.

EP Examination Report for EP Appl. No. 08869613.3 dated Jan. 20, 2011.

* cited by examiner

CHEMICAL COMPOSITION OF HYDROGELS FOR USE AS ARTICULATING SURFACES

FIELD OF THE INVENTION

The present invention relates generally to hydrogel compositions having a specified ratio of alcohol, acid, and amide functional groups contained in the hydrogel composition and specifically, to a device made of the inventive composition to be used as an implant at an articulating surface and for spinal disc repair and/or replacement.

BACKGROUND

Hydrogels are water-swellable or water-swollen materials whose structure is typically defined by a crosslinked or interpenetrating network of hydrophilic homopolymers or copolymers. The hydrophilic homopolymers or copolymers can be water-soluble in free form, but in a hydrogel they may be rendered insoluble generally due to the presence of covalent, ionic, or physical crosslinks. In the case of physical crosslinking, the linkages can take the form of entanglements, crystallites, or hydrogen-bonded structures. The crosslinks in a hydrogel provide structure and physical integrity to the polymeric network.

Hydrogels can be classified as amorphous, semicrystalline, hydrogen-bonded structures, supermolecular structures, or hydrocolloidal aggregates. Numerous parameters affect the physical properties of a hydrogel, including porosity, pore size, nature of gel polymer, molecular weight of gel polymer, and crosslinking density. The crosslinking density influences the hydrogel's macroscopic properties, such as volumetric equilibrium swelling ratio, compressive modulus, or mesh size. Pore size and shape, pore density, and other factors can impact the surface properties, optical properties, and mechanical properties of a hydrogel.

Over the past three to four decades, hydrogels have shown promise for biomedical and pharmaceutical applications, mainly due to their high water content and rubbery or pliable nature, which can mimic natural tissue. Biocompatible hydrogels can be engineered to be either degradable or resistant to degradation. An additional advantage of hydrogels, which has only recently been appreciated, is that they may provide desirable protection of drugs, peptides, and proteins from the potentially harsh environment in the vicinity of a release site.

However, typical hydrogels lack the required mechanical and frictional properties to be useful as articulating and weight-bearing mediums. Biostable hydrogels are often based on alcohol functional polymers such as hydroxymethylmethacrylates, polyvinyl alcohol, etc. These materials are known to readily absorb and release water. However, they do not have the same frictional properties as that of articular cartilage. Particularly, the degree of bound water in these types of synthetic materials is far less than that for natural cartilage.

Therefore, there is a need to develop hydrogel materials that mimic the frictional properties of natural articulating surfaces.

SUMMARY OF THE INVENTION

The present invention provides a hydrogel composition comprising at least one polymer with functional groups including alcohol groups, acid groups, and amide groups. The ratio of the functional alcohol groups to functional acid groups in the hydrogel composition ranges from about 16:1 to about 3:2.

The present invention also provides a method of repairing an articulating surface in a body. The inventive method comprises creating a hydrogel composition containing at least one polymer with functional groups including alcohol groups, acid groups, and amide groups, wherein the ratio of the functional alcohol groups to functional acid groups in the hydrogel ranges from about 16:1 to about 3:2. In one embodiment, the inventive hydrogel composition is created by blending two or more polymers to achieve the desired ratio of functional groups. In another embodiment, the inventive hydrogel composition is created by reacting at least one polymer with a reagent that results in the formation of alcohol, acid, and/or amide functional groups of the desired ratio. The method further comprises forming the composition into a hydrogel article of the approximate dimensions of the articulating surface to be repaired and replacing the damaged articulating surface with the hydrogel article.

DETAILED DESCRIPTION

The present invention provides a hydrogel composition having functional groups including alcohol groups, acid groups, and amide groups, that mimic the ratio of the functional groups found in synovial fluid components. Synovial fluid is a thick, stringy fluid found in the cavities of synovial joints and reduces friction between the articular cartilage and other tissues in joints to lubricate and cushion them during movement. Examples of synovial joints include ball and socket joints such as the shoulder and hip joints. The synovial fluid is composed primarily of glycosaminoglycans (GAG). The primary GAG component in synovial fluid is hyaluronate, comprising about 95%, with other sulphated GAGs making up the remainder. The components of synovial fluid exhibit the following ratios of functional alcohol groups to functional acid groups to functional amide groups, respectively: hyaluronate—4:1:1; chondroitin sulfate—3:2:1; keratin sulfate—4:1:1; and dermatan sulfate—3:2:1. According to the invention, by approximating the ratio of functional groups found in synovial fluid components, a hydrogel will exhibit properties similar to the synovial fluid components, in particular the frictional properties.

The present invention provides a hydrogel composition comprising at least one polymer with functional groups including alcohol groups, acid groups, and/or amide groups, wherein the ratio of the functional alcohol groups to functional acid groups in the hydrogel ranges from about 16:1 to about 3:2. In another embodiment, the ratio of the functional alcohol groups to the functional acid groups ranges from about 4:1 to about 3:2. In another embodiment, the ratio of the functional alcohol groups to the functional acid groups to the functional amide groups ranges from about 16:1:1 to about 3:2:1. In another embodiment, the ratio of the functional alcohol groups to the functional acid groups to the functional amide groups ranges from about 4:1:1 to about 3:2:1.

Examples of acid functional groups include sulfuric, sulfurous, carboxylic, sulfonamide, phosphoric, and phosphorous groups, and combinations thereof. In certain embodiments, the acid functional group has a pKa less than 9. In certain embodiments, the acid functional group is in the form of a salt and may be at least partially neutralized. In some embodiments, the salt is formed with a cationic species such as sodium, potassium, calcium, dimethyl ammonium, or lithium.

Alcohol functional groups can be denoted as R—OH and examples include phenol, allyl alcohol, vinyl alcohol, and siloxol, and combinations thereof.

Amide functional groups can be denoted $RCONR_2$ and examples of amide functional groups include primary, secondary, and tertiary amides such as acrylamide, phthalimide, carboxamide, 2-ethyl-oxazoline, benzylphthalimide, benzamide, and acetamide.

In one embodiment, the inventive composition is a blend of two or more polymers that collectively provide the ratio of functional alcohol groups to functional acid groups to functional amide groups. For instance, an amide group can come from polyacrylamide wherein each repeat unit represents 1 mole of amide group, an acid group can come from polyacrylic acid wherein each repeat unit represents 1 mole of amide group, and an alcohol group can come from polyvinyl alcohol wherein each repeat unit represents 1 mole of alcohol group. In some embodiments, at least one polymer of the inventive composition is formed of polyvinyl alcohol (PVA) or methacrylate. In one embodiment, PVA is blended with polyacrylic acid.

In some embodiments of the present invention, the blend of two or more polymers may include a hydrophilic polymer, such as PVA, and a second polymer that is a copolymer. In one embodiment, the second copolymer has hydrophobic recurring units and hydrophilic recurring units. For example, the second polymer may be polyethylene-co-vinyl alcohol. As non-limiting examples, other suitable polymers include diol-terminated polyhexamethylene phthalate and polystyrene-co-allyl alcohol. In all embodiments, the relative amount of the polymers in the blend is determined by the overall resulting ratio of functional groups present.

In one embodiment, the desired ratio of functional groups in the inventive composition is achieved by polymerization of monomers. In one embodiment, monomers may be combined and polymerized to form co- or terpolymers with the resulting composition exhibiting the required ratio of alcohol, acid, and amide functional groups. An example of a copolymer is poly-ethylene-co-vinyl alcohol, also known as "EVAL", "PEVAL" or "EVOH." Other examples of copolymers that may be suitable include polyethylene-co-acrylic acid and polyethylene-co-methacrylic acid.

In one embodiment, the desired ratio of functional groups in the inventive composition is achieved by reacting one or more polymers with a reactant that is capable of modifying the amount of alcohol functional groups, acid functional groups, and/or amide functional groups on the polymer. In one embodiment, reacting a polymer with a reactant results in the formation of a copolymer or terpolymer. An example of the formation of a terpolymer would include the polymerization of vinyl acetate with methacrylic acid and acrylamide followed by post hydrolysis to give polyvinyl alcohol-co-methacrylic acid-co-acrylamide. In another example, the terpolymer could be produced by the polymerization of vinyl pivilate with methyl methacrylate and acrylamide followed by post hydrolysis to give the polyvinyl alcohol-co-methacrylic acid-co-acrylamide polymer. In one embodiment, the reacting of one or more polymers results in one or more polymers having the desired ratio of functional groups.

In one embodiment, the inventive composition exhibiting the desired ratio of alcohol, acid, and amide functional groups is achieved by at least one of blending of one or more polymers, polymerization of one or more monomers, or reacting of one or more polymers with a reactant.

Polymeric materials that may be used to make the inventive composition include water-swellable materials and hydrogels and typically include a hydrophilic polymer. In one embodiment, the hydrophilic polymer may be polyvinyl alcohol (PVA), or derivatives thereof. By way of illustration only, other hydrophilic polymers that may be suitable include polyhydroxyethyl methacrylate, polyvinyl pyrrolidone, polyacrylamide, polyacrylic acid, hydrolyzed polyacrylonitrile, polyethyleneimine, ethoxylated polyethyleneimine, polyallylamine, or polyglycols as well as blends or mixtures of any of these hydrophilic polymers. Further examples of suitable materials to be used in the inventive composition can be found in U.S. patent application Ser. No. 11/614,389, incorporated by reference herein in its entirety.

The inventive composition may also include additional polymers, fibers, particles, peptides and proteins, such as collagen, or conventional additives such as plasticizers, components for inhibiting or reducing crack formation or propagation, components for inhibiting or reducing creep, or particulates or other additives for imparting radiopacity to the article. By way of example only, an additive for imparting radiopacity can include metal oxides, metal phosphates, and metal sulfates such as barium sulfate, barium titanate, zirconium oxide, ytterbium fluoride, barium phosphate, and ytterbium oxide. Biopolymers may also be used in certain embodiments. Suitable biopolymers include anionic biopolymers such as hyaluronic acid, cationic biopolymers such as chitosan, amphipathic polymers such as collagen, gelatin and fibrin, and neutral biopolymers such as dextran and agarose. Optionally, a radiation sensitive material such as a photoinitiator may be added to facilitate crosslinking of the inventive composition. Other optional additives include biocompatible preservatives, surfactants, colorants and/or other additives conventionally added to polymer mixtures.

Optionally, the polymeric materials, the hydrogel material, or articles of the present invention may be subjected to one or more crosslinking steps. Crosslinking may be carried out after forming the inventive composition, after shaping the inventive composition into an article, or at any other suitable point during processing.

A variety of conventional approaches may be used to crosslink the inventive composition, including, physical crosslinking (e.g., freeze thaw method), photoinitiation, irradiation and chemical crosslinking. Covalent crosslinking is a process by which individual polymer chains are irreversibly linked together and can be the result of either irradiation or chemical bonding using reagents. Reversible physical bonding forces or interactions may also occur in the polymers of the inventive composition, either alone or in combination with chemical crosslinking.

The present invention also provides a method of repairing an articulating surface in a body, in whole or in part, using a hydrogel composition containing at least one polymer with functional groups including alcohol groups, acid groups, and amide groups, wherein the ratio of the functional alcohol groups to functional acid groups in the hydrogel ranges from about 16:1 to about 3:2. In another embodiment, the ratio of the functional alcohol groups to the functional acid groups in the composition ranges from about 4:1 to about 3:2. In one embodiment, the ratio of the functional alcohol groups to the functional acid groups to the functional amide groups in the composition ranges from about 16:1:1 to about 3:2:1. In another embodiment, the ratio of the functional alcohol groups to the functional acid groups to the functional amide groups in the composition ranges from about 4:1:1 to about 3:2:1.

In one embodiment, the inventive composition is shaped into an article having the approximate dimensions of the articulating surface to be repaired, including a small damaged portion of the articulating surface or the entire articulating surface. The damaged articulating surface, in whole or in part, is then replaced with the shaped article by methods known to one skilled in the art, for instance, an orthopedic surgeon. Shaping of the article can be accomplished by various processing methods known to one skilled in the art. Processing methods to obtain a resulting article of desired shape or size may include solution casting, injection molding, or compression molding. In general, these methods may be used before or after crosslinking, as well as before or after the article is hydrated, in the case of water-swellable materials.

The article formed from the inventive composition can be used in a variety of applications, including minimally invasive surgical procedures, as known in the field. By way of example, the inventive composition can be used to provide artificial articular cartilage. In one embodiment, the composition of the present invention is used to form an artificial meniscus or articular bearing components. In another embodiment, the composition of the present invention is used to form implants employed in temporomandibular joints, in proximal interphalangeal joints, in metacarpophalangeal joints, in metatarsalphalanx joints, or in hip capsule joint repairs. In various other embodiments, the article may be a knee component replacement implant or a tibial repair implant.

The composition of the present invention can also be used to replace or rehabilitate the nucleus pulposus of an intervertebral disc. Degenerative disc disease in the lumbar spine is marked by a dehydration of the intervertebral disc and loss of biomechanical function of the spinal unit. The inventive composition can be employed in a spinal disc prosthesis used to replace a part or all of a natural human spinal disc.

In some embodiments, the article is thermoplastic. In one embodiment where a water-swellable material is used in the inventive composition, the water-swellable material may be in the form of a lyogel, which is a term generally used to described the physical state of a hydrogel material or article before the solvent used to prepare the hydrogel material is replaced with water. The thermoplastic lyogel can be melted and re-solidified without losing its water-swellable properties. The thermoplastic quality of the water-swellable article as a lyogel allows for easy processability. Upon melting, the lyogel becomes flowable and can therefore be extruded, injected, shaped, or molded.

In some embodiments, the inventive composition can be manually handled in a heated, flowable state without special precautions. Melt-processability allows the inventive composition to be manipulated so that in situ delivery and shaping can be accomplished. The heating can be accomplished with any conventional heat source that would permit the inventive composition to be heated to a temperature at which it can flow. An example of a suitable means for heating is a hot gun. The in situ delivery can be accomplished with any suitable device, such as a delivery tube or a needle. In some embodiments, the means for heating and means for delivery can be combined into one physical device. Therefore, the thermoplastic inventive composition may be directly injected into the body of a patient, to allow for in situ formation and/or hydration of the hydrogel material. Such a technique may have practical application in several minimally invasive surgical procedures, as known to one skilled in the art.

In embodiments where the inventive composition contains a hydrogel, the hydrogel may be used to release therapeutic drugs or other active agents. Hydrogels can be suitably employed in vivo to provide elution of a protein, drug, or other pharmacological agent impregnated in the hydrogel or provided on the surface of the hydrogel.

Various embodiments of the present invention are set out in the following examples.

Example 1

Blending to Achieve Desired Ratio of Alcohol, Acid, and Amide Functional Groups

An inventive composition can be derived by blending polyacrylamide, polyacrylic acid, and polyvinyl alcohol. The mixture of all three polymers may also come from blending a homopolymer with that of a copolymer as in the case of polyvinyl alcohol with polyacrylamide-co-acrylic acid. The relative quantities of each polymer to be used in the synthesis of the inventive composition requiring 100 grams of polymer is shown in Table 1.

TABLE 1

Blending of polymers to form the inventive composition

| Molar Ratio Alcohol-to-Acid-to-Amide | Poly(vinyl alcohol), g | Poly(acrylic acid), g | Poly(acrylamide), g |
|---|---|---|---|
| 16:1:0 | 90.71 | 9.29 | 0.00 |
| 3:2:0 | 47.81 | 52.19 | 0.00 |
| 16:1:1 | 83.10 | 8.51 | 8.39 |
| 3:2:1 | 38.02 | 41.51 | 20.47 |

Example 2

Blending to Achieve Required Ratio of Acid and Alcohol Functional Groups 27.28 g polyvinyl alcohol and 31 ml of DMSO blended with 12 ml of polyacrylic acid partial sodium salt (0.3 weight percent sodium, MW ~240,000, 25 weight percent in water) was added to a Haake twin screw rheometer. The materials were mixed at 120° C. for five minutes. The polyvinyl alcohol, as used, was >99% hydrolyzed with an average molecular weight of 250,000 and was obtained from Vam & Poval Co., Ltd. (Japan). The DMSO was used as received from Sigma-Aldrich and contained ≦0.4% water. The polyacrylic acid was used as received from Sigma-Aldrich (catalog number 192058). The resulting material was plastic and could be injection molded using a Battenfeld BA CD 100.

Example 3

Blending of Monomers Prior to Polymerization to Achieve Required Ratio of Functional Groups An inventive composition can be derived by blending the monomers of polyacrylamide, polyacrylic acid, and polyvinyl alcohol. In this example, the monomers vinyl acetate, acrylic acid, and acrylamide are blended. The relative quantities of each monomer to be used in the synthesis of the inventive composition requiring 100 grams of polymer is shown in Table 2. The synthesis can be done by solution, emulsion, suspension, or other polymerization techniques to form a co- or ter-polymer. Polyvinyl alcohol is derived from polyvinyl acetate. After polymerization, a hydrolysis step is required to convert the vinyl acetate into the vinyl alcohol. The hydrolysis is typically done in an alcoholic base mixture such as methanol with sodium hydroxide.

TABLE 2

Blending of monomers to form the inventive composition

| Molar Ratio Alcohol-to-Acid-to-Amide | vinyl acetate, g | acrylic acid, g | acrylamide, g |
|---|---|---|---|
| 16:1:0 | 95.02 | 4.97 | 0.00 |
| 3:2:0 | 64.18 | 35.82 | 0.00 |
| 16:1:1 | 90.59 | 4.74 | 4.67 |
| 3:2:1 | 54.54 | 30.44 | 15.01 |

The invention is further set forth in the claims listed below. This invention may take on various modifications and alterations without departing from the scope thereof. In describing embodiments of the invention, specific terminology is used for the sake of clarity. The invention, however, is not intended to be limited to the specific terms so selected, and it is to be understood that each term so selected includes all technical equivalents that operate similarly.

What is claimed is:

1. A hydrogel composition comprising at least one polymer with functional groups including alcohol groups, acid groups, and amide groups, wherein the ratio of the functional alcohol groups to functional acid groups in the hydrogel composition ranges from about 16:1 to about 3:2, in which the functional alcohol groups are from polyvinyl alcohol.

2. The composition of claim 1 wherein the ratio of the functional alcohol groups to the functional acid groups ranges from about 4:1 to about 3:2.

3. The composition of claim 1 wherein the ratio of the functional alcohol groups to the functional acid groups to the functional amide groups ranges from about 16:1:1 to about 3:2:1.

4. The composition of claim 1 wherein the ratio of the functional alcohol groups to the functional acid groups to the functional amide groups ranges from about 4:1:1 to about 3:2:1.

5. The composition of claim 1 wherein the at least one polymer comprises a blend of two or more polymers that collectively provide the ratio of functional alcohol groups to functional acid groups to functional amide groups.

6. The composition of claim 1 wherein the hydrogel composition is formed by at least one of blending two or more polymers, polymerizing at least one monomer, or reacting at least one polymer.

7. The composition of claim 1 wherein the acid functional group is selected from the group consisting of sulfuric, sulfurous, carboxylic, sulfonamide, phosphoric, and phosphorous, and combinations thereof.

8. The composition of claim 1 wherein the acid functional group has a pKa less than 9.

9. The composition of claim 1 wherein the acid functional group is in the form of a salt and is at least partially neutralized.

10. The composition of claim 9 wherein the salt is formed with a cationic species and includes sodium, potassium, calcium, dimethyl ammonium, or lithium.

11. The composition of claim 1 wherein the amide functional group is selected from the group consisting of acrylamide, pyrrolidone, phthalimide, carboxamide, 2-ethyl-oxazoline, benzylphthalimide, benzamide, and acetamide, and combinations thereof.

12. A method of repairing an articulating surface in a body with a hydrogel composition comprising at least one polymer with functional groups including alcohol groups, acid groups, and amide groups, wherein the ratio of the functional alcohol groups to functional acid groups in the hydrogel composition ranges from about 16:1 to about 3:2, in which the functional alcohol groups are from polyvinyl alcohol, the method comprising:
creating the hydrogel composition in a step comprising blending two or more polymers, reacting at least one polymer with a reagent, or polymerizing at least one monomer to provide the hydrogel composition;
forming the hydrogel composition into a hydrogel article of the approximate dimensions of the articulating surface to be repaired; and
replacing the damaged articulating surface with the hydrogel article.

13. The method of claim 12 wherein the ratio of the functional alcohol groups to the functional acid groups ranges from about 4:1 to about 3:2.

14. The method of claim 12 wherein the ratio of the functional alcohol groups to the functional acid groups to the functional amide groups ranges from about 16:1:1 to about 3:2:1.

15. The method of claim 12 wherein the ratio of the functional alcohol groups to the functional acid groups to the functional amide groups ranges from about 4:1:1 to about 3:2:1.

16. The composition of claim 3, in which the functional alcohol groups are from the polyvinyl alcohol, the functional acid groups are from polyacrylic acid, and the functional amide groups are from polyacrylamide.

17. The method of claim 14, in which the hydrogel composition is created by combining polyvinyl alcohol, polyacrylamide and polyacrylic acid, and wherein the functional alcohol groups are from the polyvinyl alcohol, the functional acid groups are from polyacrylic acid, and the functional amide groups are from polyacrylamide.

18. The hydrogel composition of claim 1 wherein said composition mimics the frictional properties of human synovial fluid components.

19. The method of claim 12 wherein said hydrogel composition mimics the frictional properties of human synovial fluid components.

\* \* \* \* \*